United States Patent
Lowe et al.

(10) Patent No.: US 9,777,264 B2
(45) Date of Patent: Oct. 3, 2017

(54) MATERIALS AND METHOD FOR IMMOBILIZING, ISOLATING, AND CONCENTRATING CELLS USING CARBOXYLATED SURFACES

(71) Applicant: Qiagen Gaithersburg, Inc., Gaithersburg, MD (US)

(72) Inventors: Brian Lowe, Olney, MD (US); Irina Nazarenko, Gaithersburg, MD (US); Szymon Rus, Washington, DC (US)

(73) Assignee: QIAGEN GAITHERSBURG, INC., Gaithersburg, MD (US)

( * ) Notice: Subject to any disclaimer, the term of this patent is extended or adjusted under 35 U.S.C. 154(b) by 483 days.

(21) Appl. No.: 13/667,674

(22) Filed: Nov. 2, 2012

(65) Prior Publication Data

US 2013/0115590 A1    May 9, 2013

Related U.S. Application Data

(60) Provisional application No. 61/555,349, filed on Nov. 3, 2011.

(51) Int. Cl.
| | | |
|---|---|---|
| C12N 13/00 | (2006.01) | |
| C12N 11/08 | (2006.01) | |
| C12N 11/10 | (2006.01) | |
| C12N 11/14 | (2006.01) | |

(52) U.S. Cl.
CPC .............. *C12N 13/00* (2013.01); *C12N 11/08* (2013.01); *C12N 11/10* (2013.01); *C12N 11/14* (2013.01)

(58) Field of Classification Search
None
See application file for complete search history.

(56) References Cited

U.S. PATENT DOCUMENTS

| | | | |
|---|---|---|---|
| 5,849,517 A * | 12/1998 | Ryan | 435/40.51 |
| 7,439,016 B1 | 10/2008 | Anthony et al. | |
| 7,812,144 B2 | 10/2010 | Karlsen | |
| 2005/0032038 A1 | 2/2005 | Fisher et al. | |
| 2006/0051809 A1 | 3/2006 | Nazarenko | |
| 2006/0141450 A1* | 6/2006 | Zhang et al. | 435/5 |
| 2007/0109898 A1 | 5/2007 | Kasai | |

(Continued)

FOREIGN PATENT DOCUMENTS

| | | |
|---|---|---|
| EP | 1 806 410 A2 | 7/2007 |
| EP | 2 184 368 A1 | 5/2010 |

(Continued)

OTHER PUBLICATIONS

Thermo Scientific (retrieved on Jan. 30, 2015 from: http://www.thermoscientific.com/content/dam/tfs/SDG/CDD/CDD%20Marketing%20Material/Particles%20Documents/Particle/%20Technology%20Product%20Catalog.pdf).*

(Continued)

*Primary Examiner* — Joseph G Dauner
(74) *Attorney, Agent, or Firm* — McBee Moore Woodward & Vanik IP, LLC

(57) ABSTRACT

The present disclosure relates to immobilization of a cell using a carboxylated surface by contacting the carboxylated surface with a sample comprising the cell for a sufficient time to permit the cell to bind to the carboxylated surface. The immobilized cell may then be separated from the remainder of the sample and further manipulated to isolate, concentrate, and/or analyze the cell or a component thereof.

24 Claims, 5 Drawing Sheets

(56) References Cited

U.S. PATENT DOCUMENTS

2007/0154884 A1 7/2007 Lorincz
2010/0311039 A1 12/2010 Lowe et al.

FOREIGN PATENT DOCUMENTS

| | | |
|---|---|---|
| JP | 200400508019 A | 3/2004 |
| WO | 01/96608 A1 | 12/2001 |
| WO | 2004087950 A2 | 10/2004 |
| WO | 2006/124771 A2 | 11/2006 |
| WO | 2007/130519 A2 | 11/2007 |
| WO | 2008/139938 A1 | 11/2008 |
| WO | 2009/015159 | 1/2009 |
| WO | 2009/057993 A1 | 5/2009 |
| WO | 2010/004251 A1 | 1/2010 |
| WO | 2010/127228 A1 | 11/2010 |

OTHER PUBLICATIONS

PreservCyt (retrieved on Jan. 30, 2015 from: https://www.testmenu.com/crittenton/TestDirectory/SiteFile?fileName=sidebar%5CPreseryCyt.pdf).*
Bioclone. Retrieved on Jul. 22, 2015 from the internet: https://web.archive.org/web/20101214073503/http://www.bioclone.us/carboxyl-terminated-magnetic-beads-particle-resin-matrix.html.*
MagnaBind. Retrieved on Jul. 22, 2015 from the internet: https://www.funakoshi.co.jp/data/datasheet/PCC/21353.pdf.*
International Search Report and Written Opinion of the International Searching Authority Based on Application No. PCT/US2012/063385 Malied Feb. 5, 2013.
Schwalbe et al.; "Selective Reduction of the Interaction of Magnetic Nanoparticles With Leukocytes and Tumor Cells by Human Plasma"; Journal of Magnetism and Magnetic Materials, No. 1; May 1, 2005; pp. 433-437; Elsevier Science Publishers; Amsterdam, NL; vol. 293.
International Preliminary Report on Patentability dated May 6, 2014, issued in Application No. PCT/US2012/063385, English translation.
Coutlee et al., "Nonisotopic Detection of RNA in an Enzyme Immunoassay Using a Monoclonal Antibody against DNA-RNA Hybrids." Analytical Biochemistry 181, 153-162 (1989).
Lowe et al.; "A Hybrid-Capture Assay to Detect HPV MRNA Ratios in Cervical Specimens"; Journal of Virological Methods; vol. 179; No. 1; Jan. 2012; pp. 142-147.
International Search Report Based on Application No. PCT/US2012/026380 Mailed Oct. 15, 2012.
English Translation of Second Chinese Office Action dated Jan. 31, 2013, issued in Application No. 201080018737.6
International Search Report Based on Application No. PCT/US2012/020684 Mailed Oct. 25, 2012.
Clad et al.; "Performance of the APTIMA High-Risk Human Papillomavirus MRNA Assay in a Referral Population in Comparison With Hybrid Capture 2 and Cytology"; Journal of Clinical Microbiology; Mar. 2011; LNKD-Pubmed:21191046; vol. 49; No. 3; Dec. 29, 2010; pp. 1071-1076; Abstract.
Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.
Han et al.; "Simultaneous Amplification and Identification of 25 Human Papillomavirus Types With Templex Technology"; Journal of Clinical Microbiology 200611 US LNKD-DOI:10.1128/JCM.01762-06; vol. 44; No. 11; Nov. 2006; pp. 4157-4162; Abstract.
Database EMBL [Online]; Jul. 19, 2007; "Sequence 25 From Patent EP1806410"; XP002675256; Retrieved From EBI Accession No. EMBL:CS642417; Database Accession No. CS642417; The Whole Document.
Database EMBL [Online]; Dec. 14, 2010; "Sequence 26 From Patent U.S. Pat. No. 7,812,144"; XP00267527; Retrieved From EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.
Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.
Database Geneseq [Online]; Apr. 1, 2010; "HPV16 E7 Gene Forward RT-PCR Primer SEQ ID 49"; XP002675260; Retrieved From EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, SEQ ID No. 37"; XP002675261; Retrieved From EBI Accession No. GSN:ADX15568; Database Accession No. ADX15568; Sequence.
Phillips et al., "Simultaneous Detection of C282Y and H63D Hemochromatosis Mutations by Dual-color Probes" Molecular Diagnosis. vol. 5, No. 2: 107-116, (Jun. 2000).

* cited by examiner

MATERIALS AND METHOD FOR IMMOBILIZING, ISOLATING, AND CONCENTRATING CELLS USING CARBOXYLATED SURFACES

CROSS-REFERENCE TO RELATED APPLICATIONS

This application claims priority to U.S. Provisional Patent Application Ser. No. 61/555,349, filed Nov. 3, 2011, the contents of which are hereby incorporated by reference in their entirety.

BACKGROUND

A. Field of the Invention

The present invention relates to materials in methods for use in concentrating and/or isolating cells from a sample using carboxylated surfaces.

B. Brief Description of Related Art

Carboxylated surfaces have found multiple uses in the biotechnological arts.

Frequently, the surfaces are used to isolate specific biomolecules. For example, WO 2007-004687 discloses the formation of agglutinates of lipoproteins, other than a specific lipoprotein fraction, using magnetic nanoparticles which have anionic functional groups, such as a carboxylic acid group, on their surfaces.

Carboxylated surfaces also have been used as supports for biomolecule- and biomaterial-specific ligands, which may be used to immobilize the biomolecule or biomaterial. In the typical scenario, the carboxyl group is activated, for example, using a carbodiimide. The activated carboxyl is then reacted with a reactive group (such as an amine) in an entity capable of binding to a target cell or class of target cells, such as an antibody, thereby immobilizing the entity to the surface. The cell may then be bound to the surface via an interaction between the immobilized entity and the cell. For example, in WO 2007-095279 carboxy-modified nanoparticles coated with DNA aptamers having a high affinity for a target cell are used to immobilize the cell and separate it from the sample by flow cytometry. In U.S. Pat. No. 7,713,627, "probe-bonded particles" are disclosed for use in separating bacteria, viruses, and cells. The "probe" specific for the target may be attached to the particle via chemical reaction with a surface functionalized with a carboxylic acid-bearing group. In EP 1118676, microorganisms are isolated using binding between the microorganism and a ligand, such as a carbohydrate to which the microorganism is known to bind, a nutrient for the microorganism, or an iron chelating compound.

Others have described the use of carboxylated surfaces to directly isolate viruses from biological samples. For example, US 2003-0087284 discloses the use of particles coated with at least one cationic group and at least one anionic group to bind, separate, and detect viruses.

SUMMARY OF THE INVENTION

The present disclosure relates to immobilization of a cell using a carboxylated surface.

A method of immobilizing a cell is disclosed, comprising contacting a carboxylated surface with a sample, the sample comprising the cell and a fixative, for a sufficient time to permit the cell to bind to the carboxylated surface.

A method of isolating a cell from a sample is disclosed comprising: (a) contacting a carboxylated surface with a sample comprising the cell and a fixative agent under conditions sufficient to induce binding between the cell and the surface; and (b) separating the surface from the sample, thereby isolating the cell.

A method of isolating a biomolecule from a cell is also disclosed, the method comprising: (a) contacting a carboxylated surface with a sample comprising the cell under conditions sufficient to induce binding between the cell and the surface; (b) separating the surface from the sample, thereby isolating the cell; and (c) lysing the cell, thereby releasing the biomolecule.

A method of determining the presence of a biomolecule in a sample is also disclosed, the method comprising: (a) contacting a carboxylated surface with a sample comprising the cell under conditions sufficient to induce binding between the cell and the surface; (b) separating the surface from the sample, thereby isolating the cell; (c) lysing the cell, thereby releasing the biomolecule into a lysate; and (d) detecting the biomolecule in the lysate.

A method of determining the presence of a nucleic acid in a sample is also disclosed, the method comprising: (a) contacting a carboxylated surface with a sample comprising the cell under conditions sufficient to induce binding between the cell and the surface; (b) separating the surface from the sample, thereby isolating the cell; (c) lysing the cell, thereby releasing the nucleic acid; and (d) detecting the nucleic acid by a method comprising generating a DNA:RNA hybrid between the nucleic acid and a nucleic acid probe specific for the nucleic acid.

A method of concentrating a cell in a sample is also disclosed, said method comprising: (a) contacting a carboxylated surface with the sample under conditions sufficient to induce binding between the cell and the surface; and (b) removing at least a portion of the sample that is not bound to the surface, thereby concentrating the cell.

Also disclosed is a complex between a cell and a carboxylated surface in the presence of a fixative agent.

Also disclosed is a carboxylated surface for use in the methods disclosed herein.

BRIEF DESCRIPTION OF THE DRAWINGS

FIG. 1 is a bar graph comparing HPV16 nucleic acid recovery using carboxylate beads to concentrate the cell ("COOmag") compared to centrifugation ("MC"). SiHa cells (either 300,000 or 30,000) were used as a source of HPV16, spiked in either HPV-negative clinical samples or clean PRESERVCYT® liquid cytology medium. The y-axis represents a signal (in relative light units ("RCU")) directly correlating to the concentration of the HPV 16 nucleic acid.

FIG. 2 is a bar graph comparing HPV16 nucleic acid recovery using carboxylate beads to concentrate the cell ("COOmag") compared to centrifugation ("MC"). SiHa cells (either 300,000 or 30,000) were used as a source of HPV16, spiked in either HPV-negative clinical samples or clean PRESERVCYT® liquid cytology medium. The y-axis represents a signal (in RCU) directly correlating to the concentration of the HPV 16 nucleic acid.

FIG. 3 is a bar graph comparing HPV16 nucleic acid recovery using different amount of carboxylate beads (10 μl and 5 μl) and different incubation times (1, 10, 15 and 30 min.) to concentrate the cell.

FIG. 4 is a bar graph comparing HPV16 nucleic acid recovery when various volumes (50, 100, and 200 μl) of the supernatant removed after immobilization of the cells was reserved and added back to the lysate before being assayed. "PC Sup" indicates that an indicated volume of a supernatant was added before the HC2™ assay. "STM+/DNR" indicates positive controls using an indicated volume of a 2:1 mixture of STM/DNR in place of the added supernatant.

Figure 8:
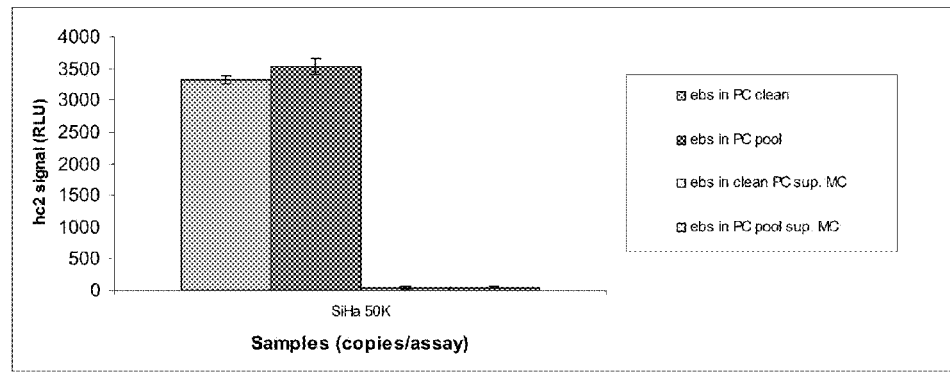

FIG. 8 is a bar graph comparing recovery of nucleic acid from heat inactivated *Chlamydia trachomatis* elementary bodies spiked into clean PRESERVCYT™ ("ebs in PC clean") or HPV-negative cervical specimen pool in PRESERVCYT™ ("ebs in PC Pool"), using a carboxylated bead to concentrate the elementary bodies before nucleic acid isolation and analysis. Comparative examples without the bead concentration are indicated by "ebs in PC clean sup MC" and "ebs in PC Pool sup MC".

Figure 9:
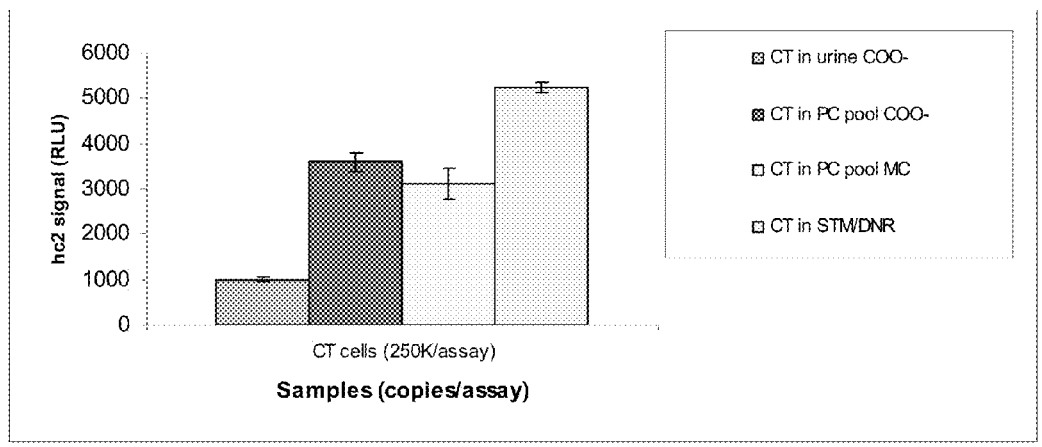

FIG. 9 is a bar graph comparing recovery of nucleic acid from heat inactivated *Chlamydia trachomatis* elementary bodies were spiked into HPV-negative cervical specimen pool in PRESERVCYT™ ("ebs in PC Pool") or fresh urine, and carboxylated beads were to concentrate the elementary bodies before nucleic acid isolation and analysis. Comparative examples without the bead concentration are indicated by "PC Pool sup MC". *Chlamydia trachomatis* elementary bodies added directly to a 2:1 mixture of STM and DNR were used as a positive control ("STM/DNR").

DETAILED DESCRIPTION OF THE INVENTION

The present disclosure includes methods, compositions, reagents, systems, and kits related to immobilization of cells using a carboxylated surfaces. The methods, compositions, reagents, systems, and kits are useful for, for example, laboratory research and clinical diagnostic purposes, including but not limited to isolation of biomolecules from cells for use in the detection and identification of pathogenic organisms and the detection of a genetic predisposition to a particular disease.

Immobilizing the Cell

In an aspect, a method of immobilizing a cell is disclosed, said method comprising contacting a sample comprising the cell with a carboxylated surface under conditions sufficient to induce binding between the cell and the surface. In principle, any cell can be used. In an aspect, the cell is a mammalian cell. In another aspect, the mammalian cell is a human cervical epithelial cell. In another aspect, the cell is a unicellular organism, such as a bacterium of the genus *Mycobacterium, Chlamydia, Staphylococcus,* or *Neisseria*; or a protozoa of the genus *Trichomonas*; or a yeast of the genus *Saccharomyces* or *Candida*. In another aspect, the bacterium is of the genus *chlamydia*, for example, in the form of an elementary body.

As used herein, the terms "carboxylate compound", "carboxylate group", and "carboxylate moiety" shall refer to any compound or portion thereof comprising at least one free carboxylic acid (COOH), carboxylate anion (COO$^-$), or carboxylate salt [—COO$^{(-)}$X$^{(+)}$].

As used herein, the term "carboxylated surface" shall refer to a surface of a solid or quasi-solid, the surface comprising a free carboxylic acid group [—COOH], carboxylate anion [—COO$^{(-)}$], or carboxylate salt [—COO$^{(-)}$X$^{(+)}$].

The term "surface" as used herein in particular refers to the portion of a solid phase which comes into contact with a solution when the solid phase is contacted therewith. The solid phase provides the surface that provides, e. g. carries, the carboxylate group, carboxylate anion, or carboxylate salt. Suitable solid phases may be made of or may comprise in particular at their surface a material selected from the following group:

a material comprising or consisting of silicon such as silica and polysilicic acid materials, quartz, borosilicates, silicates, diatomaceous earth or glasses, a material comprising or consisting of a polymer such as poly(meth)acrylate, polyurethane, polystyrene, polystyrol, polyacrylamide, a divinylbenzene polymer, a styrene divinylbenzene polymer, polyethylene, polypropylene, polyvinylidene fluoride, polyacrylonitrile, polyvinylchloride, polyacrylate, polyacrylamide, polymethacrylate or a methyl methacrylate polymer;

a material comprising or consisting of a polysaccharide such as agarose, cellulose, dextrans or sepharose;

a material comprising or consisting of a mineral;

a material comprising or consisting of a metal oxide such as aluminum oxide, magnesium oxide, titanium oxide or zirconium oxide;

a material comprising or consisting of a metal such as gold or platinum; and a material comprising or consisting of a derivative of the foregoing.

Furthermore, the solid phase may also comprise more than one of the above described materials. In an aspect, at least the surface comprising the carboxylate moieties is composed of one of the described materials or a mixture thereof. Also any solid phase suitable for ion exchange chromatography may be used as solid phase to provide the surface that comprises, e.g. is functionalized with, carboxylate groups.

Exemplary formats of the solid phase include but are not limited to particles such as beads, membranes, filters, plates, columns and dipsticks. According to one aspect, the surface comprising carboxylate moieties is provided by a vessel, for example the inner surface of a vessel that is intended to receive the sample. The inner surface or portions thereof can be functionalized, e.g. coated, with carboxylate moieties. Examples of respective vessels include but are not limited to microtubes and wells of a microplate. In this aspect, the cells bind due to the provided carboxylate moieties to the inner surface of the vessel or well and are thereby collected.

According to an exemplary aspect, the surface is provided by a solid phase that can be provided as suspension and can be separated from a liquid phase. When contacted with a liquid phase such as for example a cell containing liquid based cytology medium, the surface comprising the carboxylate moieties is in contact with the liquid phase in order to allow cell binding. In an aspect, the surface comprising carboxylate moieties is provided by particles which comprise carboxylate moieties at their surface. The particles may have an average size that is selected from a range of 100 nm to 50 μm, 200 nm to 40 μm, 300 nm to 35 μm, 400 nm to 30 μm, 450 nm to 25 μm, 500 nm to 20 μm, 550 nm to 15

µm, 600 nm to 12.5 µm, 650 nm to 10 µm, 700 nm to 7.5 µm, 750 nm to 5 µm, 800 nm to 3.5 µm, 800 nm to 3 µm, 800 to 2.5 µm, 800 nm to 2 µm and 800 nm to 1.5 µm. Particles of the respective sizes and in particular of a smaller size such as 5 µm or less, 2.5 µm or less or 1.5 µm or less are easy to handle and can be well resuspended in the cell sample. Furthermore, respective small particles provide a large surface area that can bind and accordingly can efficiently collect the cells from the remaining sample such as e.g. a liquid-based cytology collection medium. Suitable materials for providing or making the particles are described above. The particles may also comprise more than one of the above described materials, e.g. comprising two or more layers comprising or consisting of different materials to provide the particle body.

In an aspect, magnetic particles are used to provide a carboxylated surface that binds cells. Using magnetic particles has the advantage, that they can be processed and moved by the aid of a magnetic field. The magnetic particles can for example have superparamagnetic, paramagnetic, ferrimagnetic or ferromagnetic characteristics. The magnetic particles may comprise a magnetic material that is incorporated in the particles and/or is associated with the particles. To avoid leaching of the magnetic material, the magnetic material may be completely encapsulated e. g. by the material providing the surface such as e.g. silica, polysilicic acid, glass or a polymeric material such as polyacrylate.

Numerous suitable solids and quasi-solids are well-known in the art, including but not limited to surfaces useful in cation exchange chromatography. The solid or quasi-solid should be of such a character that it can be placed in suspension in, and separated from, a liquid phase. Moreover, the solid or quasi-solid should be of such a character that, when contacted with a liquid phase, the surface comprising the carboxylate-containing compound is in contact with the liquid phase. Exemplary solid or quasi-solid surfaces include, but are not limited to polycarbonate and/or magnetic beads, including paramagnetic, diamagnetic, ferromagnetic, ferrimagnetic, and diamagnetic beads; columns; plates; filter paper; polydimethylsiloxane (PDMS); and dipsticks. In an exemplary aspect, the carboxylated surface comprises a magnetic bead. Exemplary magnetic beads include those which are described in the German patent application DE 10 2005 058 979.9. Such magnetic beads are commercially available.

In an exemplary aspect, the surface is coated with a carboxylated polymer. Examples of carboxylated polymers which are suitable as coating material are described in detail in the German patent application DE 10 2005 040 259.3. Examples of compounds which may be bound to the surface are glycine, aspartic acid, 6-aminocaproic acid, NTA (nitrilotriacetic acid), polyacrylic acid (PAA), diglyme (diethylene glycol dimethyl ether), or combinations of these, without being limited thereto.

In an aspect, the carboxylated surface has a negative overall charge, preferably a weakly negative overall charge. In a further aspect, the carboxylated surface comprises a carboxyl content as determined by conductometric titration with sodium hydroxide of: at least 0.1 mEq/g; at least 0.2 mEq/g; at least 0.3 mEq/g; at least 0.4 mEq/g; from about 0.1 to about 0.7 mEq/g; from about from about 0.1 to about 0.6 mEq/g; from about 0.1 to about 0.5 mEq/g; from about 0.2 to about 0.7 mEq/g; from about 0.2 to about 0.6 mEq/g; from about 0.2 to about 0.5 mEq/g; from about 0.3 to about 0.7 mEq/g; from about 0.3 to about 0.6 mEq/g; from about 0.3 to about 0.5 mEq/g; from about 0.4 to about 0.7 mEq/g; from about 0.4 to about 0.6 mEq/g; or from about 0.4 to about 0.5 mEq/g.

In a further aspect, the carboxylated surface may comprise additional anionic functional groups, such as phosphonate and/or sulfate groups.

In another aspect, a carboxylated surface suitable for use in cation exchange chromatography is used. Such surfaces are well known in the art, such as, for example, carboxylate-modified superparamagnetic microspheres, such as those sold under the name SERADYN® DS-MGCM beads. In a further aspect, the surface is suitable for use in cation exchange chromatography, but not carboxylated chromatography.

In an aspect, binding of the cell to the carboxylated surface is not mediated by a ligand-receptor interaction or an antibody-antigen interaction. As such, a carboxylated surface comprising at least one compound that is not modified with a receptor ligand or an antibody capable of binding the cell may be used. In a further aspect, the cell is immobilized by a direct association between the carboxylate group.

Any sample may be used in which cells may be present, including, without limitation: a specimen or culture (e.g., cellular and tissue cultures) including clinical and laboratory biological samples; food and agricultural samples; and forensic samples, including urine, semen, hair, blood, skin, and saliva samples. Samples may be from any mammal, including a human, and explicitly include fluid, solid (e.g., stool) or tissue, as well as liquid and solid food and feed products and ingredients such as dairy items, meat and meat by-products, and waste. Explicitly included are samples taken directly from a mammal, as well as samples that have been stored in a preservative, including but not limited to paraffin-embedded tissue samples and cellular and tissue samples stored in a liquid-based cytology medium.

According to one aspect, the carboxylated surface is added to a liquid sample comprising the cell. In an aspect, the particle comprising the carboxylated surface is added to the liquid sample in a volume to achieve a particle concentration after resuspension that lies in a range selected from: at least 10 µg/ml, at least 20 µg/ml; at least 30 µg/ml; at least 40 µg/ml; at least 50 µg/ml; 10 µg/ml to 1000 µg/ml; 10 µg/ml to 500 µg/ml; 10 µg/ml to 300 µg/ml; 10 µg/ml to 200 µg/ml; 20 µg/ml to 1000 µg/ml; 20 µg/ml to 500 µg/ml; 20 µg/ml to 300 µg/ml; 20 µg/ml to 200 µg/ml; 30 µg/ml to 1000 µg/ml; 30 µg/ml to 500 µg/ml; 30 µg/ml to 300 µg/ml; 30 µg/ml to 200 µg/ml; 40 µg/ml to 1000 µg/ml; 40 µg/ml to 500 µg/ml; 40 µg/ml to 300 µg/ml; 40 µg/ml to 200 µg/ml; 40 µg/ml to 1000 µg/ml; 40 µg/ml to 500 µg/ml; 50 µg/ml to 300 µg/ml; and 50 µg/ml to 200 µg/ml.

In an aspect, the liquid sample comprises at least one fixative agent. In an aspect, the sample comprises a cross-linking and/or non-cross-linking fixative agent. Cross-linking fixatives function by making chemical bonds between proteins in the tissue sample, leading to their precipitation and immobilization within the tissue. Exemplary crosslinking fixatives include, but are not limited to, glyoxal formaldehyde and paraformaldehyde. Non-cross-linking fixatives do not chemically alter the proteins in the sample; rather they simply precipitate them where they are found in the tissue sample. Non-cross-linking fixatives include ethanol, acetone, methanol and mixtures thereof.

In an aspect, the liquid sample is in a liquid cytology medium. In an aspect, the liquid cytology medium comprises at least one component selected from the group consisting of a cross-linking fixative, a precipitating fixative, and an oxidizing agent. Exemplary cross-linking fixatives include aldehydes, such as formaldehyde and glutaraldehyde. Exemplary precipitating fixatives include alcohols, such as methanol and ethanol, and acetone. Exemplary oxidizing agents include osmium tetroxide, potassium dichromate, chromic acid, and potassium permanganate. In an aspect, the liquid cytology medium comprises an alcohol. In an aspect, the alcohol is selected from the group consisting of ethanol and methanol. In an aspect, the liquid cytology medium comprises an aldehyde. In an aspect, the aldehyde is selected from the group consisting of formaldehyde and glutaraldehyde. In an aspect, the liquid cytology medium comprises both an aldehyde and an alcohol. Commercially available liquid cytology media include, but are not limited to PRESERVCYT® (Hologic, Inc., Bedford, Mass.) (a methanol-based liquid cytology medium comprising ~42% methanol; ~5 mM EDTA, pH 4.5); DIGENE® Specimen Transport Medium (Qiagen Gaithersburg, Inc., Gaithersburg, Md.) (a guanidinium-based specimen transport medium); and SUREPATH™ (Becton, Dickinson and Company, Franklin Lakes, N.J.) (a liquid cytology medium comprising ~22% ethanol and a trace cell fixative/cross-linker (formaldehyde-like), pH 7). In an aspect, the pH of the liquid cytology medium is in a range selected from the group consisting of: not more than 9; not more than 8; not more than 7; from 2 to 9; from 2 to 8; from 2 to 7; from 3 to 9; from 3 to 8; from 3 to 7; from 4 to 9; from 4 to 8; from 4 to 7. In an aspect, the pH of the liquid cytology medium is adjusted to improve immobilization of the cell to the carboxylated surface.

In an aspect, the liquid sample is urine.

In an aspect, the cells are brought into contact with the carboxylated surface in the presence of the liquid cytology medium or urine over a sufficiently long period of time, i.e. a period of time which suffices to allow the cells to bind/attach themselves to the carboxylated surface. Such a period of time should be at least 30 s, preferably at least 1 min, further preferably at least 3 min, further preferably at least 10 minutes.

Concentrating a Cell from the Sample and/or Isolating the Cell from the Sample

In an aspect, the carboxylated surface may be used to concentrate or isolate the cell. In an aspect, a method is provided comprising: (a) immobilizing the cell to a carboxylated surface as set forth above; and (b) separating the carboxylated surface with the cell bound thereto from at least a portion of the sample, thereby concentrating and/or isolating the cell.

Different modes of operations are feasible in order to separate the surface with the bound cells from the sample.

In an aspect, a vessel is used, wherein the inner wall of the vessel is at least partially functionalized with carboxylated moieties as described herein, the remaining sample can be discarded by decanting or it can be removed by aspiration or similar methods. The bound cells remain associated to the inner surface of the vessel due to the carboxylated moieties. Respective separation steps can be performed using a robotic system.

As another example, particles comprising carboxylated moieties are used to provide the carboxylated surface. If the particles are non-magnetic they can be collected for example by filtration or sedimentation which can according to one aspect be assisted by centrifugation. It is preferred though to use magnetic particles, because the magnetic particles including the bound cells can be processed easily by the aid of a magnetic field, e.g. by using a permanent magnet. This aspect is preferred as it is compatible with established robotic systems capable of processing magnetic particles. Here, different robotic systems exist in the prior art that can be used in conjunction with the present invention to process the magnetic particles to which the cells were bound. According to one aspect, the magnetic particles are collected at the bottom or the side of the reaction vessel and the remaining liquid sample is removed from the reaction vessel, leaving behind the collected magnetic particles to which the cells are bound. Removal of the remaining sample can occur by decantation or aspiration. Such systems are well known in the prior art and thus need no detailed description here.

In an alternative system that is known for processing magnetic particles the magnet which is usually covered by a cover or envelope plunges into the reaction vessel to collect the magnetic particles. The magnetic particles that carry the bound cells can then be transferred for example into a new reaction vessel e.g. comprising a resuspension solution, preferably a denaturing composition as will be described in the following. As respective systems are well-known in the prior art and are also commercially available (e.g. QIAsymphony; QIAGEN), they do not need any detailed description here.

In a further alternative system that is known for processing magnetic particles, the sample comprising the magnetic particles can be aspirated into a pipette tip and the magnetic particles can be collected in the pipette tip by applying a magnet e.g. to the side of the pipette tip. The remaining sample can then be released from the pipette tip while the collected magnet particles which carry the bound cells remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

It is within the scope of the present invention and preferred to contact the bound cells after step b) with a liquid composition. This aspect has the advantage that it may inter alia support the collection of the cells if magnetic particles are used, in particular if a robotic system is used for collecting the magnetic particles wherein the magnet plunges into the reaction vessel. By contacting the collected cells which are still bound to the magnetic particles with a liquid composition, it is ensured in this aspects that the particles are efficiently removed from the magnet and are redispersed in the liquid composition. However, contacting the collected cells with a liquid composition has additional general advantages also when using other magnetic separation systems or other carboxylated surfaces as described herein. The liquid composition is compatible with the subsequent downstream processing, for example, when forming double stranded DNA:RNA hybrids as described below. The liquid composition may be added to the collected cells that are bound to the carboxylated surface, e.g. it may be added to the magnetic particles carrying the bound cells or vice versa. According to one aspect contacting the carboxylated surface carrying the bound cells with the liquid composition results in that the collected cells are at least partially released and thus eluted from the carboxylated surface. If desired, the carboxylated surface can then be separated from the released cells. Here, any mode of separation is feasible and suitable modes include but are not limited to collecting the liquid composition comprising the released cells e.g. by aspiration or, which is feasible if magnetic particles are used, collecting and separating the magnetic particles from the remaining liquid composition comprising the released cells using a magnetic field. However, as is shown by the examples, it is not mandatory to remove the carboxylated surface prior to steps c) and d) and this is a particular advantage of the present invention as this again saves handling steps. The cells may even remain bound to the carboxylated surface as long as the nucleic acids are released therefrom.

Releasing an Entity from the Immobilized Cell

In an aspect, an entity may be released from a cell that has been immobilized as described above, optionally after the cell has been concentrated and/or isolated from the rest of the sample. By way of example and not limitation, the entity may include, but is not limited to: a biomolecule, such as nucleic acids (including but not limited to DNA and RNA), peptides (including but not limited to oligopeptides and polypeptides), lipids, sugars, et cetera; a virus or viral particle; an organelle or other subcellular structure; and a microorganism, such as bacteria, mycobacteria, protozoa, and fungi. Methods of releasing the foregoing entities are well known in the art.

In an aspect, the entity is a biomolecule selected from the group consisting of peptides and nucleic acids. In an aspect, the biomolecule is a cell-surface peptide and is released without lysing the cell, such as by extraction from the plasma membrane, elution of a ligand from a cell surface receptor, or enzymatic release of a protein anchored to the plasma membrane.

In another aspect, the biomolecule is an intracellular, and is released by lysing the cell. Any manner of lysing the cell can be used in the disclosed method, including without limitation: mechanical lysis, such as by sonication or cytolysis; and chemical lysis, including use of detergents such as 3-[(3-cholamidopropyl)dimethylammonio]-1-propanesulfonate (sold commercially as CHAPS®); octylphenoxypolyethoxyethanol (also known as NONIDET P-40® or IGEPAL CA-630®); deoxycholate; $C_{14}H_{22}O(C_2H_4O)_n$ (sold commercially as TRITON® X-100); sodium dodecyl sulfate (sold commercially as SDS); and/or polysorbate surfactants (sold commercially as TWEEN®). In a further aspect, lysis is performed in the presence of heat.

In a further aspect, a nucleic acid, is released by a method comprising: (b) isolating or concentrating the cell as set forth above; (c) contacting the cell with a liquid composition that lyses the cell, thereby releasing the nucleic acid into a lysate, and (d) optionally, denaturing the released nucleic acid. According to one aspect, the collected cells are lysed by contacting them with a liquid composition.

In an aspect, the liquid composition for lysing the cells comprises a chaotropic agent. Any chaotropic agent can be used for this purpose that causes disorder in a protein or nucleic acid by, for example, but not limited to altering the secondary, tertiary or quaternary structure of a protein or a nucleic acid. Preferably, a chaotropic salt is used. The chaotropic salt preferably comprises guanidinium, thiocyanate, isothiocyanate, perchlorate, trichloroacetate and/or trifluoroacetate as chaotropic ion. Preferably, the chaotropic agent is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluroacetate and urea. Also a mixture of chaotropic agents can be used. Preferably, guanidinium hydrochloride, guanidinium thiocyanate or guanidinium isothiocyanate is used as chaotropic agent in the composition that assists the release of the nucleic acids in step c). The liquid composition may comprise the chaoptropic agent, which preferably is a chaotropic salt as mentioned above, in a concentration that lies in a range selected from about 0.1 M up to the saturation limit, about 0.2 M to 8 M, about 0.3 M to 4 M, about 0.4 M to 3 M, about 0.5 M to 2.5 M, about 0.6 M to about 2 M, about 0.6 M to about 1.5 M and 0.6 M to about 1 M. Preferably, the liquid composition is a solution such as a lysis buffer.

According to one aspect, the liquid composition for lysing the cells comprises a chelating agent, preferably EDTA. A chelating agent is an organic compound that is capable of forming coordinate bonds with metals through two or more atoms of the organic compound. Suitable chelating agents include, but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred aspect, EDTA is used. As used herein, the term "EDTA" indicates inter alia the EDTA portion of an EDTA compound such as, for example, $K_2EDTA$, $K_3EDTA$ or $Na_2EDTA$.

According to one aspect, the liquid composition for lysing the cell may comprise a detergent. The detergent may be non-ionic, ionic, anionic, cationic or zwitterionic.

In an aspect, the liquid composition for lysing the cells may comprise a preservative such as sodium azide. Furthermore, the liquid composition for lysing the cells may comprise a buffering agent. Preferably, a biological buffer such as HEPES, MES, MOPS, TRIS, BIS-TRIS Propane and others is comprised in the composition. Preferably, a Tris buffer is used.

In an aspect, the released nucleic acid is also denatured. This can be achieved e.g. by adding a denaturation agent such as a base and/or heating as will be described in the following. For cases in which the released nucleic acid is double stranded and is to be hybridized to a nucleic acid probe, it is preferred that the double-stranded target nucleic acid is converted to a be at least partially single stranded to make the nucleic acids accessible to hybridization.

In an aspect, the liquid composition for lysing the cells has an alkaline pH value to achieve or support the denaturation of the released nucleic acids. According to one aspect, the liquid composition has a pH value that is selected from a pH value of 10 or more, a pH value of 11 or more, a pH value of 11.5 or more, a pH value of 12 or more, a pH value of 12.5 or more, a pH value of 12.75 or more, a pH value of 13 or more and a pH value of 13.25 or more. A high alkaline pH value supports the release of the nucleic acids and furthermore, denatures the released nucleic acids, thereby preparing the nucleic acids for detection (d1). This aspect is particularly preferred if the target nucleic acid is DNA because such basic pH will both nick and degrade a majority of the internal RNA in the specimen. In an aspect, the denaturation is supported by heating as will be described below. In addition, alkaline treatment can disrupt interactions between peptides and nucleic acids to improve accessibility of the target nucleic acid and degrade protein. Furthermore, alkaline treatment of proteins effectively homogenizes the specimen to ensure reproducibility of analysis results for a given sample. It can also reduce the viscosity of the sample to increase kinetics, homogenize the sample, and reduce background by destroying any endogenous single stranded RNA nucleic acids, DNA-RNA hybrids or RNA-RNA hybrids in the sample. It also helps inactivate enzymes such as RNases and DNases that may be present in the sample. One skilled in that art would appreciate that if RNA is the target nucleic acid (as opposed to DNA), different reagents may be preferable. For establishing an alkaline pH value as described above, a base, preferably a chemical base such as e.g. sodium or potassium hydroxide can be added, respectively may be comprised in the liquid composition.

Using a strong alkaline liquid composition as described above is particularly suitable if the target nucleic acid is DNA. If the target nucleic acid is RNA, more moderate conditions are preferred in order to preserve the integrity of the RNA. E.g. the liquid composition may have a pH value of 7.5 to 10, 8 to 9.5 or 8.5 to 9.

The liquid composition for lysing the cells can be provided by one composition, e.g. one solution or may be prepared by contacting the cells with two or more separate compositions. According to one aspect, the collected cells are contacted with two or more separate compositions in order to provide the release and denaturation conditions described above. According to one aspect, two or more compositions are mixed to provide a liquid composition as described above prior to contracting said composition with the carboxylated surface to which the cells are bound (preferably magnetic particles). According to one aspect, a first composition comprises the chaotropic agent and optionally the other components described above (e.g. the composition STM can be used as first composition, see examples) and a separate second composition comprises the denaturation agent (e.g. DNR as second composition, see examples). In an aspect, said second composition is an alkaline solution. Any alkali that can bring the liquid composition that results from the mixing of the first and second composition to a pH range described above is suitable. Suitable concentrations of alkali include from about 1.0 N to about 2.0 N or from about 1.25 N to about 1.75 N. Without being limited, suitable alkali include NaOH and KOH. Mixing the two (or more) compositions together provides the liquid composition that assists the release and denaturation of the nucleic acids and thus provides the conditions described above and in particular establishes the alkaline pH value described above. Preparing the liquid composition by mixing two or more separate compositions to establish the conditions described above is preferred and it is in particular preferred to add the denaturation agent as described above separately.

According to one aspect, the surface is provided by magnetic particles, and the collected cells that are bound to the magnetic particles are contacted with an amount of the liquid composition described above that is selected from 25 μl to 500 μl, 30 μl to 400 μl, 35 μl to 300 μl, 40 μl to 250 μl, 50 μl to 200 μl, 60 μl to 175 μl, 70 μl to 150 μl, 80 μl to 125 μl and 85 μl to 100 μl. According to one aspect, the liquid composition is added in a volume to achieve a particle concentration after resuspension that lies in a range selected from 2000 μg/ml to 15000 μg/ml, 2500 μg/ml to 12500 μg/ml, 3000 μg/ml to 10000 μg/ml; 3500 μg/ml to 9500 μg/ml, 4000 μg/ml to 9000 μg/ml, 4500 μg/ml to 8750 μg/ml and 5000 μn/ml to 8500 μg/ml.

Instead of or in addition to the denaturation agent described above, other methods of denaturation may be employed such as utilizing a heating step, for example, heating the sample to at least 80° C. or at least 95° C. to separate the nucleic acid strands. Adding an alkaline denaturation agent, which can be comprised in the liquid composition as described above, and performing a heating step is preferred to efficiently denature the released nucleic acids.

According to one aspect, after the cells were contacted with the liquid composition for lysing the cells, the resulting mixture is heated to assist the denaturation of the nucleic acids. Preferably, said mixture is heated to at least 55° C., preferably at least 60° C. Suitable temperature ranges include 55° C. to 90° C., preferably 60° C. to 85° C. and more preferred 65° C. to 80° C. Preferably, heating occurs for at least 30 min, preferably at least 35 min, more preferred at least 40 min. Suitable time periods can be selected from 30 min to 150 min, 35 min to 130 min, 40 min to 120 min and 45 min to 100 min. The described time and temperature conditions shall provide an efficient denaturation of the nucleic acids in an acceptable amount of time, while leaving the target nucleic acid in a suitable condition for carrying out (d1). The suitable time period also depends on the processed sample. E.g. when processing cell containing samples comprising specific fixatives such as SUREPATH samples, longer incubation times of 90 min (or longer if desired) at a temperature of at least 60° C., preferably at about 65° C. are preferred. When processing cell-containing samples that do not comprise cross-linking fixatives such as PRESERVCYT samples, shorter incubation times of e.g. 45 min (or longer if desired) at a temperature of at least 60° C., preferably at about 65° C. are sufficient. Suitable time periods can also be determined by the skilled person. It will be readily understood by one of ordinary skill in the art that longer periods of incubation at lower temperatures, or shorter periods of incubation at higher temperatures, may be balanced to provide a similar effect to the conditions described herein. The release of the nucleic acids can also be assisted by shaking E.g. the sample treated with the liquid composition described above can be mixed by hand mixing or mechanical shaking at about 800 rpm, about 900 rpm, about 1000 rpm, between about 600 and about 1000 rpm, or between about 600 and 1200 rpm.

According to one aspect, the sample mixture comprising the liquid composition for lysing the cells, the cells and optionally the carboxylated surface, e.g. the magnetic particles, or an aliquot of said mixture is transferred into a new vessel, preferably a multi-well device such as a 96 well plate, prior to heating. This aspect is advantageous as it can be easily integrated in established assay work-flows for generating and isolating DNA:RNA hybrids and also automated processing systems as therein respective multi-well devices are processed and accordingly, existing equipment can be used.

After performing the above, a sample is obtained which comprises the released nucleic acid. Said sample optionally also comprises the carboxylated surface, e.g. magnetic particles if the magnetic particles were not separated prior to or during the isolation.

The sample obtained after may be stored e.g. at 4° C. or below prior to performing subsequent processing steps, if any.

Detecting a Released Nucleic Acid

In an aspect, a method for detecting a target nucleic acid in a sample is disclosed, said method comprising: (c) releasing the nucleic acid from the cell as described above; (d) optionally denaturing the released nucleic acid; and (e) detecting the released nucleic acid.

Any method of detecting the nucleic acid may be used, including gel electrophoresis, PCR-related techniques including reverse transcriptase PCR and real time PCR, sequencing, sub-cloning procedures, Southern blotting, northern blotting, fluorescent in situ hybridization, and various mutational analyses including HYBRID CAPTURE™ and multiplex analysis. In one exemplary aspect, a nucleic acid comprising a specific sequence may be detected by hybridizing it to a nucleic acid probe complementary to the specific sequence. In one aspect, the nucleic acid probe is bound to a solid phase or adapted to be bound to a solid phase. In another aspect, hybridization of the nucleic acid probe to the nucleic acid molecule results in a DNA:RNA hybrid between the probe and the nucleic acid molecule. The resulting hybrid may then be bound by an antibodies known to bind specifically to DNA:RNA hybrids ("DNA:RNA-binding antibody"), which in turn may be bound to a solid phase or adapted to be bound to a solid phase. In either case, hybridization of the probe with the nucleic acid results in the nucleic acid being associated with a solid phase, which may then be separated from the lysate using mechanical means. By way of example and not limitation, such methods are described in U.S. Pat. No. 6,228,578 and U.S. patent application Ser. No. 12/695,071, the contents of which are incorporated in their entirety by reference. Exemplary DNA:RNA-binding antibodies include, but are not limited to, those disclosed in U.S. Pat. Nos. 4,732,847 and 4,865,980, the contents of which are incorporated herein by reference in their entireties. In other exemplary methods, the nucleic acid is detected by, inter alia, amplifying the nucleic acid.

Exemplary amplification methods include, but are not limited to, polymerase chain reaction ("PCR"), reverse transcriptase PCR ("RT-PCR"), real time PCR, real-time RT-PCR.

In a further aspect, an automated method for screening clinical samples for a disease state is provided, said method comprising: (a) immobilizing a cell comprised in the samples to the surface comprising carboxylated moieties as set forth above; (b) isolating or concentrating the cell as set forth above; (c) lysing the cells to create a lysate as set forth above; (d) optionally denaturing the released nucleic acid; and (e) detecting the presence of a target nucleic acid in the lysate, wherein the presence or absence of the target nucleic acid in the lysate is indicative of the disease state. Any detection method compatible with automation may be used. By way of example and not limitation, the detection method may comprise hybridizing a nucleic acid probe to the nucleic acid from the lysate. By way of example and not limitation, hybridization results in a DNA:RNA hybrid. In a further aspect, the DNA:RNA hybrid is detected by binding an antibody specific for DNA:RNA hybrids to the DNA:RNA hybrid between the nucleic acid probe and the nucleic acid from the lysate.

Detecting a Released Nucleic Acid Using Double Stranded Nucleic Acid Hybrids

In an aspect, detection comprises generation of a double stranded nucleic acid hybrid between the target nucleic acid and a nucleic acid probe specific therefor. In an aspect, the nucleic acid hybrid is a DNA:RNA hybrid.

According to one aspect, detection comprises:
(e1) contacting the released and optionally denatured target nucleic acid with one or more probes specific for the target nucleic acid under conditions that allow the probes and target nucleic acid to hybridize forming double-stranded nucleic acid hybrids; and
(e2) detecting the presence or absence of double-stranded nucleic acid hybrids.

In an aspect, the double stranded nucleic acid hybrids are detected by a method comprising:
(e2α) capturing the double stranded nucleic acid hybrids to a solid support;
(e2β) optionally separating the double-stranded nucleic acid hybrids bound to the solid support from un-bound nucleic acids; and
(e2γ) detecting the presence or absence of double-stranded nucleic acid hybrids.

In another aspect:
(e2α) the double stranded nucleic acid hybrids are captured to the solid support by contacting the double stranded hybrids with a first binding agent that is bound to or adapted to be bound to the solid phase to form a double-stranded nucleic acid/first binding agent complex; and
(e2γ) the presence or absence of double-stranded nucleic acid hybrids is detected by (a) binding said double-stranded nucleic acid/first binding agent complex with a further binding agent that is labelled with a detectable marker to form a double-stranded nucleic acid hybrid/first binding agent/labelled binding agent complex; (b) optionally washing the double-stranded nucleic acid hybrid/first binding agent/labelled binding agent complex; and (c) detecting the presence or absence of the label of the further binding agent thereby indicating the presence or absence of the target nucleic acid.

In the foregoing aspects, the carboxylated surface preferably is disposed on a magnetic particle, which magnetic particle may optionally be present throughout the detection.

In one aspect, detection comprises the use of an analyzer comprising: (1) a heating element; and (2) a device for detecting a detectable signal, such as a fluorimeter or a luminometer.

In the foregoing methods, after release and optional denaturation of the nucleic acids as is described above, the target nucleic acids are contacted with one or more probes under conditions suitable for the one or more probes to hybridize to the target nucleic acid to form a double-stranded nucleic acid hybrid. The probe is preferably a polynucleotide probe. The probe can be full length, truncated, or synthetic DNA or full length, truncated, or synthetic RNA. Furthermore, probes comprising RNA and DNA nucleotides or comprising modified nucleotides and/or analogs of nucleotides can be used, as long as a hybrid is formed. If the target nucleic acid is DNA, then preferably the probe is RNA and if the target nucleic acid is RNA, then preferably the probe is DNA. Accordingly, a RNA/DNA hybrid is preferably formed. The probes are designed to hybridize or bind with the target nucleic acid molecules.

In one aspect, the probes are capable of hybridizing or binding to HPV and HPV high risk variants. In an additional aspect, the probes are specific for HPV and HPV high risk variants. High risk (HR) probes can include probes for HPV high risk types 16, 18, 31, 33, 35, 39, 45, 51, 52, 56, 58, 59, 66, 68 and 82. The probes may vary in amount from about 7.5 ng to about 60 ng per HPV type per assay, or from about 20 ng to about 45 ng per HPV type per assay, or about 30 ng of probe for each HPV type per assay is used. Thus, in one aspect the HR probes consist of or consist essentially of one or more probes for HPV high risk types 16, 18, 31, 33, 35, 39, 45, 51, 52, 56, 58, 59, 66, 68, and 82 or low risk HPV types 6, 11, 40, 43, 53, 61, 67, 69, 70, 71, 72, 81, and 83. The RNA probes may be short synthetic RNA probes that specifically bind only to the target nucleic acid molecule.

In a non-limiting aspect, the one or more probe used is capable of hybridizing or binding to target nucleic acid molecules that are at least 70 percent, at least 80 percent, at least 85 percent, at least 90 percent, at least 95 percent, at least 96 percent, at least 97 percent, at least 98 percent, at least 98 percent, at least 99 percent, or 100 percent identical to nucleic acid molecules associated with HPV, genetic variants of HPV, HPV DNA of a high risk HPV type, or HPV RNA of a high risk HPV type, or any one of high risk HPV types 16, 18, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83. In another aspect, the one or more probes used is complementary to HPV, genetic variants of HPV, HPV DNA of a high risk HPV type, HPV RNA of a high risk HPV type, or any one of high risk HPV types 16, 18, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83. Also DNA or RNA fragments of the target nucleic acids can be used.

According to one aspect, the denatured sample is neutralized prior to or during the addition of the probes if denaturation occurred under alkaline conditions. According to one aspect, the one or more probes are diluted in a probe diluent that also can act as a neutralizing hybridization buffer. This aspect is advantageous in order to neutralize the alkaline pH value that was used in step c) to release and denature the nucleic acids. The probe diluent used for DNA or RNA probes will differ due to the different requirements necessary for DNA versus RNA stability. For example, if the probes are RNA, it is preferred to neutralize the sample first and then add the one or more probes or alternatively, add the RNA probe and a neutralizing agent (probe diluent) to the sample at the same time as strong alkaline pH values can destroy RNA. The probe diluent can be used to dissolve and dilute the probe and also help restore the sample to about a neutral or weakly alkaline pH, e.g., about pH 6 to about pH 9, preferably 6.5 to 8, more preferred 6.5 to about 7.5 to provide a more favorable environment for hybridization. Sufficient volume of probe diluent, e.g. one-half volume of the sample, may be used to neutralize a base-treated sample.

In an aspect, the probe diluent comprises a buffer, polyacrylic acid, NaOH and sodium azide. The probe diluent may comprise acetic acid. In one aspect, the probe diluent comprises 2.2 M BES (N,N-Bis(2-hydroxyethyl)-2-aminoethanesulfonic acid), 2.6 percent polyacrylic acid (PAA), 0.7 N NaOH and 0.05 percent sodium azide. The probe diluent may contain from about 1.2 M to about 2.6 M BES, from about 1.5 M to about 2.5 M BES; from about 1.75 M to about 2.25 M BES; from about 2 M to 2.4 M BES, or about 2.2 M BES, as well as any number within the recited ranges. In one aspect the probe diluent may contain from about 2 percent to about 3.0 percent PAA or, as well as any number within the recited ranges. In another aspect, the PAA concentration is from about 2.2 percent to about 2.7 percent. In yet another aspect, the PAA concentration is about 2.6 percent. In a further aspect the probe diluent may contain from about 0.6 N to about 0.8 N NaOH, for example, about 0.7 N NaOH. The concentration of NaOH generally increases as the amount of BES increases.

For large probes, a heated alkaline solution may be added to the sample, then probe diluent may be added to the sample at room temperature, and then the sample may be reheated. Such a process can inhibit secondary structure from forming. Binding agents such as antibodies tend to bind to structures with secondary structure. When using non-full length probes such as truncated or synthetic probes, heating the solutions or sample may not be necessary because secondary structures issues are not present. In an aspect, the sample is not heated when used with truncated or synthetic probes. After treatment with the denaturation reagent, an aliquot of neutralization buffer, in an aspect the probe diluent described, in which the one or more probes are dissolved, can be added to the sample under appropriate conditions to allow hybridization or binding of the probe and the target nucleic acid to occur. The neutralization buffer may contain a single buffering salt. In an aspect, the neutralization buffer does not contain more than a single buffering salt. The hybridization condition is sufficient to allow the one or more polynucleotide probes to anneal to a corresponding complementary nucleic acid sequence, if present, in the sample to form a double-stranded nucleic acid hybrid.

Hybridization conditions suitable for the particular probes and diluents used are employed. For example, the probes and sample nucleic acids can be incubated for a hybridization time, preferably at least about 5 to about 120 minutes, about 10 to about 100 minutes, or from about 20 to about 80 minutes, or from about 30 minutes to about 60 minutes, as well as any number within the recited ranges sufficient to allow the one or more polynucleotide probes to anneal to a corresponding complementary target nucleic acid sequence. The hybridization conditions can include a hybridization temperature of at least about 55° C., at least about 60° C., preferably from about 60° C. to about 75° C., preferably 65° C. to about 70° C. as well as any number within the recited ranges. For a given target nucleic acid and a given probe, one of ordinary skill in the art can readily determine desired hybridization conditions and hybridization times by routine experimentation. One of ordinary skill in the art will further appreciate that the time and temperature of hybridization must be optimized, one with respect to the other. Without being limited, stringent hybridization conditions may be controlled by increasing the temperature, increasing the ionic conditions to above 0.5 M (for example, NaCl), or reducing the concentration of PAA. As a non-limiting example, stringent hybridization conditions may include performing a hybridization reaction at elevated temperatures, such as of at least about 65° C.

After the one or more probes were allowed to hybridize to the target nucleic acid molecule and to form a double-stranded nucleic acid hybrid, the hybrid is captured by a molecule that binds to the double-stranded nucleic acid hybrid formed. Such a molecule is referred to herein as binding agent. Thereby, a double-stranded nucleic acid hybrid/binding agent complex is formed. Binding agents specific for the double stranded nucleic acid hybrids include, but are not limited to, monoclonal antibodies, polyclonal antibodies, proteins such as but not limited to RNAse H, nucleic acids including but not limited to aptamers, or sequence specific nucleic acids. In one aspect an antibody binding the formed double-stranded nucleic acid hybrid is used as binding agent, respective antibodies are also known as anti-hybrid antibodies. Accordingly, the double-stranded nucleic acid hybrids formed in accordance with the present invention can be captured and detected using antibodies or antibody fragments that are specific to double-stranded nucleic acid hybrids. Subsequently, we will describe suitable and preferred aspects by referring to antibodies. However, said description equally applies to antibody fragments such as Fab fragments capable of binding the hybrids or other suitable binding agents.

The antibody is specific to double-stranded hybrids, such as but not limited to RNA/DNA hybrids; DNA/DNA hybrids; RNA/RNA hybrids; and mimics thereof, where mimics refer to molecules that behave similarly to RNA/DNA, DNA/DNA, or RNA/RNA hybrids. The anti-double-stranded nucleic acid hybrid antibody, i.e., the anti-hybrid antibody that is utilized will depend on the type of double-stranded nucleic acid hybrid formed. In one aspect, the anti-hybrid antibody is immunospecific to RNA/DNA hybrids. It will be understood by those skilled in the art that either polyclonal or monoclonal anti-hybrid antibodies can be used and/or coupled and/or immobilized on a support in the present method as described below. In one aspect, monoclonal antibodies support high stringency incubation temperatures during the capture step. The first and further binding agents, which preferably are antibodies may be the same for capture and detection or may be different from each other. In one aspect, the first and further binding agent (which can be labelled, see below), which preferably are both monoclonal antibodies, used for capture and/or detection are the same and are specific for RNA-DNA hybrids. As described above, also suitable as binding agents are immunofragments or derivatives of antibodies that are specific for double-stranded hybrids where such fragments or derivatives contain the binding regions of the antibody.

In an aspect of the present invention, a monoclonal anti-RNA/DNA hybrid antibody derived from a hybridoma cell line is used. Such hybridoma cell lines are described in U.S. Pat. No. 4,865,980, U.S. Pat. No. 4,732,847, and U.S. Pat. No. 4,743,535. Hybrid-specific monoclonal antibodies may also be prepared using techniques that are standard in the art. The hybrid-specific monoclonal antibody may be used for both capturing and detecting the target nucleic acid. Also other binding agents suitable of specifically binding the formed hybrid can be used.

In one aspect, a first anti-hybrid binding agent such as an anti-hybrid antibody is immobilized onto a support using techniques that are standard in the art. Examples of suitable immobilization technologies include covalent linkages or adsorption, for example, protein-protein interactions, protein-G beads, biotin-streptavidin interaction, EDAC to link to a carboxyl or tosyl group, etc., or hybridization directly onto the solid support using, for example, sequence specific nucleic acids in an affinity column.

Supports include but are not limited to reaction vessels, including microtiter plates wherein one or more wells are functionalized with the molecule that binds the hybrid, preferably an anti-hybrid antibody, particles, magnetic particles, columns, plates, filter paper and dipsticks. Any support can be used as long as it allows removal, e.g. extraction of a liquid phase. Magnetic particles are useful in that they can be left in the solution and the liquid phase can be extracted or decanted, if a magnetic field is applied to immobilize the particles or the magnetic particles with the bound hybrid can be removed using a system as described above. Particles that are small and have a high surface area are preferable, such as particles about 0.5 µm to 10 µm, 0.75 µm to 7.5 µm, 0.75 µm to 5 µm, 0.75 µm to 2.5 µm and most preferred 1 µm in diameter. However, when using magnetic particles as solid support for the first binding agent that binds the hybrid, it is preferred to perform a final magnetic separation step prior to performing (d2) in order to ensure that the magnetic particles do not interfere with the detection.

Preferably, the support that is used for immobilising the first binding agent which binds the generated hybrid is a reaction vessel. Preferably, the support is provided by a multi-well device such as a microtiter plate, wherein the wells are at least partially functionalized with the first binding agent. This aspect is advantageous, as it allows to easily remove the particles that were used for binding the cells in the course of the assay, if said particles were not separated prior to (d1). The generated hybrid is captured by the binding agent and thus is immobilized to the reaction vessel, so that the remaining sample including the particles that were used for cell binding can be easily removed e.g. by aspiration and/or washing.

The hybrids are incubated with the anti-hybrid binding agent attached to the support for a sufficient amount of time to allow capture of the double-stranded nucleic acid hybrids by the immobilized anti-hybrid binding agent. Thereby, a double-stranded nucleic acid hybrid/solid support complex is formed, which also comprises the first binding agent that is used for capturing the hybrid. As described above, in a preferred aspect, the support is a reaction vessel, preferably a microtiter plate functionalized with one or more anti-hybrid binding agents such as anti-hybrid antibodies. The anti-hybrid antibody may be monoclonal or polyclonal. In one aspect the antibody is monoclonal. In one aspect, the antibody is coupled to the support by an 1-ethyl-3-[3-dimethylaminopropyl] carbodiimide hydrochloride (EDAC) linker.

In one aspect, the support is a polystyrene bead. In an aspect, the support or bead coupled to the binding agent, which preferably is an antibody, is diluted in a bead dilution buffer. The bead dilution buffer is helpful in minimizing protein denaturation on the bead. One example of a bead dilution buffer comprises 6 percent casein, 100 mM TrisHCl, 300 mM NaCl, and 0.05 percent sodium azide.

In an aspect, the support coated with the anti-hybrid antibody is incubated with the sample. Incubation may be performed at room temperature or at elevated temperatures. The incubation time can range from about 5 to about 120 minutes, about 10 to about 100 minutes, or from about 20 to about 80 minutes, or from about 30 minutes to about 60 minutes, as well as any number within the recited ranges sufficient to allow capture. The same incubation times are suitable if the first binding agent that is used for binding the formed hybrid is not bound to a solid support. The sample can be shaken during said incubation. It will be understood by those skilled in the art that the incubation time, temperature and/or shaking conditions can be varied to achieve alternative capture kinetics as desired.

Following binding and thus capture of the target nucleic acid/probe hybrid, the captured hybrid may be separated from the rest of the sample. Separation is particularly easy if the first binding agent is immobilized to a solid support. In this case, the unbound sample can e.g. simply be aspirated as is also described in the examples. According to one aspect, one or more washing steps are performed to wash away non-captured nucleic acids and sample remainders. As described above, if the particles that were used for binding the cells are still present during the generation and capture of the hybrid, they will at least be partially removed during said separation step. Advantageously, it is not necessary to specifically remove the particles e.g. by the aid of a magnet in case of magnetic particles as they will be automatically removed when separating the sample remainders. This saves handling steps.

According to one aspect, a further binding agent is used. The further binding agent may comprise a detectable label. The further binding agent is used to allow detecting the presence of double-stranded nucleic acid hybrids. The further binding agent can be bound directly or indirectly to the complex that is formed when the first binding agent binds and thus captures the formed hybrid, thereby providing a double-stranded nucleic acid hybrid/first binding agent/labelled binding agent complex or a double-stranded nucleic acid hybrid/solid support/labelled binding agent complex if the first binding agent was immobilized to a solid support. In one aspect, the further binding agent comprises a label that must react with a substrate to provide a signal that can be detected. The further binding agent may be dissolved in a suitable buffer. In one aspect the buffer comprises 100 mM TrisHCl, pH 7.4, 0.5 M NaCl, 0.1 mM $ZnCl_2$, 1.0 mM $MgCl_2$, 0.25 percent Tween 20, 0.2 mg/ml RNase A, 4 percent hydroxypropyl-b-cyclodextrin (cyclodextrin), 30 percent bead dilution buffer as discussed previously, 0.05 percent goat IgG, 0.05 percent sodium azide. Preferably, the further binding agent is an antibody or fragment thereof, preferably a monoclonal antibody.

According to one aspect, the further binding agent comprises a detectable label and binds to the double-stranded nucleic acid hybrid. Alternatively, the further binding agent which comprises a detectable label binds the first binding agent. Alternatively, the formed double-stranded nucleic acid hybrids can be detected with a second binding agent that is not directly labelled. In this aspect, a second binding agent is used which may bind to the double stranded nucleic acid hybrid or to the first binding agent and said second binding agent can be bound by a further binding agent which comprises a detectable label. For example, the second binding agent can be a mouse immunoglobulin that is detected by a labelled third antibody, e.g. a goat anti-mouse antibody.

In an aspect, the binding reaction of the labelled binding agent to the complex comprising the captured hybrid takes place at room temperature. In an aspect, the binding reaction takes place at room temperature for between about 15 minutes and 120 minutes, 20 minutes and 100 minutes, 25 minutes and 80 minutes, 30 minutes and 60 minutes or 30 minutes and 45 minutes. The binding reaction may take place at room temperature or at elevated temperatures.

It will be understood by those skilled in the art that any detectable label such as, but not limited to, an enzyme, radioactive molecule, fluorescent molecule, or metal particle such as gold particle can be used. In certain aspects, the detectable label is alkaline phosphatase. Methods of conjugating a label to an antibody are known. For example, an antibody can be reduced with dithiothreitol (DTT) to yield monovalent antibody fragments. The reduced antibody can then be directly conjugated to maleinated alkaline phosphatase by the methods of Ishikawa et al, J. Immunoassay 4:209-237 (1983) and Means et al, Chem. 1: 2-12 (1990), the contents of each of which are incorporated herein by reference in its entirety, and the resulting conjugate can be purified by HPLC. The conjugate may also be purified using any type of size-exclusion chromatography. One benefit of purification is that the conjugates of one protein to one antibody can be separated from those conjugates with other ratios of protein to antibody.

Following binding with the further binding agent comprising a detectable label, the sample can be washed with a wash buffer. The wash buffer may contain one or more detergents or may be free of a detergent. If the wash buffer contains a detergent, the detergent preferably is an ionic or a non-ionic detergent. One example of a non-ionic detergent is Triton-X. The detergent may be present in the wash buffer at a concentration of about 0.05 percent to about 1.5 percent, or from about 0.075 percent to about 1.0 percent, or from about 0.1 percent to about 0.75 percent, or about 0.5 percent or any number within the recited ranges. One example of a suitable wash buffer comprises 40 mM Tris, pH 8.2, 100 mM NaCl, 0.5 percent Triton-X 100 and 0.05 percent sodium azide.

The sample may be washed with the wash buffer from one to ten times, or from three to seven times, or from four to six times, or five times, or any number within the recited ranges. The sample may also be washed with a single wash buffer or with multiple wash buffers. Each wash may use the same wash buffer or a different wash buffer. For example, a detergent-containing wash buffer may be used for one wash while a detergent-free wash buffer may be used for another wash. In an aspect, one of the wash buffers does not include Triton.

Performing said one or more washing steps has the advantage that any remaining traces of magnetic particles that were used for binding the cells can be washed away efficiently and thus are removed prior to performing detection. The particles can be particularly easily washed away if they have a size of 5 µm or less, preferably 2.5 µm or less.

The label present on the further binding agent is detected to thus indicate the presence or absence of the target nucleic acid molecule. Methods for detecting various labels are known in the art. For example, colorimetry, radioactive, surface plasmon resonance, or chemiluminescence methods are described by e.g., Coutlee et al., J. Clin. Microbiol. 27:1002-1007 (1989), the contents of which are incorporated herein by reference in its entirety.

For example, a bound alkaline phosphatase conjugate can be detected by chemiluminescence with a reagent such as a LUMI-PHOS 530 reagent (Lumigen, Detroit, Mich.) or DR2 (Applied Biosystems, Foster City, Calif.) using a detector such as an FVLUMINA luminometer (Source Scientific Systems, Inc., Garden Grove, Calif.), an OPTOCOMP I Luminometer (MGM Instruments, Hamden, Conn.), or the like, such as a Veritas Microplate Luminometer by Turner Biosystems. Multiple detection techniques can also be used in sequence or in parallel. For example, the conjugate may be detected by chemiluminescence and fluorescence. In another aspect, the conjugate can be detected by chemiluminescence.

As described herein, detection of the label is indicative of the presence of one or more of the target nucleic acid molecules in the sample that are complementary to the one or more probes. Following washing (see above), the sample is suspended in a detection buffer that for example, contains the substrate for the label on the labelled binding agent.

One reason why the presence of HPV or other target nucleic acid molecules can be determined in short periods of time is because the method does not require an amplification of the target nucleic acid molecule prior to detection. Instead of target amplification, signal amplification may be used to accurately detect the presence of HPV or other target nucleic acid molecules. In an aspect, the methods of the present invention may include a signal amplification step. In an aspect, the methods of the present invention do not include a target amplification step and in particular do not include a PCR amplification step in (d1). In another aspect, the methods of the disclosure may include a signal amplification step and no target nucleic acid amplification step.

The present disclosure also provides methods and assays for detecting cancer, for example cervical cancer, by detecting the presence of a target nucleic acid molecule, such as HPV, in a sample using the method discussed above.

It will be understood to those skilled in the art that the detection can be carried out on a number of platforms including, but not limited to, tubes, dipsticks, microarrays, microplates, 384 well plates, other microliter plates and microfluidic systems.

In an exemplary aspect, the target nucleic acid is derived from a pathogen such as a microorganism or virus. In a further example, the nucleic acid is derived from a virus. In a further aspect, the viral nucleic acid is a virally-derived DNA molecule association with the cell in an intact virus or a viral caspid; maintained in the cell episomally; or integrated in a cellular DNA molecule, such as a chromosome of the cell. In a further aspect, the viral nucleic acid is an mRNA encoded by a viral gene or a cDNA molecule derived from such an mRNA. In a further aspect, the target nucleic acid is derived from a human papillomavirus. In a further aspect, the automated method is a method of screening clinical samples for the presence of a high-risk human papillomavirus.

In one aspect, the target nucleic acid molecules are at least 70 percent, at least 80 percent, at least 85 percent, at least 90 percent, at least 95 percent, at least 96 percent, at least 97 percent, at least 98 percent, at least 98 percent, at least 99 percent, or 100 percent identical to nucleic acid molecules associated with or comprised in any one of cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen, other viral, bacteria, mycobacteria or plasmodia, for example cytomegalovirus HPV, (CMV), herpes, HIV, H1N1, *chlamydia*, gonorrhea, *Neisseria gonorrhoeae* (GC), *Chlamydia trachomatis* (CT), *Trichomonas vaginalis, Staphylococcus aureus*, tuberculosis, SARS-associated coronavirus or influenza.

In one aspect, the target nucleic acid molecules are human papillomavirus (HPV) and include genetic variants of HPV. A variant includes polymorphisms, mutants, derivatives, modified, altered, or the like forms of the target nucleic acid. In one aspect, the target nucleic acid is an HPV nucleic acid. In another aspect, the HPV nucleic acid is HPV DNA of a high risk HPV type. In another aspect, the HPV nucleic acid is HPV RNA of a high risk HPV type. In another aspect the target nucleic acids are any one of high risk HPV types 16, 18, 26, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83. In one aspect, the target nucleic acid molecule is at least 70 percent, at least 80 percent, at least 85 percent, at least 90 percent, at least 95 percent, at least 96 percent, at least 97 percent, at least 98 percent, at least 98 percent, at least 99 percent, or 100 percent identical to nucleic acid molecules associated with any one of HPV, genetic variants of HPV, HPV DNA of a high risk HPV type, or HPV RNA of a high risk HPV type. In another aspect the target nucleic acids are at least 70 percent, at least 80 percent, at least 85 percent, at least 90 percent, at least 95 percent, at least 96 percent, at least 97 percent, at least 98 percent, at least 98 percent, at least 99 percent, or 100 percent identical to nucleic acid molecules associated with any one of high risk HPV types 16, 18, 26, 31, 33, 35, 39, 45, 51, 52, 56, 58, 59, 66, 68, and 82 or any one of low risk HPV types 6, 11, 40, 43, 53, 61, 67, 69, 70, 71, 72, 81, and 83.

The target nucleic acid molecule may be DNA or RNA. In one aspect, the target nucleic acid to be detected is DNA (e.g., HPV genomic DNA or cDNA) or RNA (e.g., mRNA, ribosomal RNA, nuclear RNA, transfer RNA, viral RNA, heterogeneous nuclear RNA, small non-coding RNA, siRNA, miRNA), wherein the one or more polynucleotide probes are polyribonucleotides or polydeoxyribonucleotides, respectively or mixtures thereof. The probes may also comprise modified nucleotides. When the target nucleic acid molecule is DNA, the polynucleotide probe is preferably RNA and when the target nucleic acid is RNA, the polynucleotide probe is preferably DNA. However, a DNA probe can be used with DNA target nucleic acid molecule and an RNA probe can be used with RNA target nucleic acid molecule. In a preferred aspect, the double-stranded nucleic acid hybrids are DNA-RNA hybrids formed by hybridization of target DNA and probe RNA, and can be detected using an antibody that is immunospecific to RNA-DNA hybrids.

In a preferred aspect, the target nucleic acid is derived from a pathogen such as a microorganism or virus. In a further example, the target nucleic acid is derived from a virus. In a further aspect, the viral nucleic acid is a virally-derived DNA molecule and can be present in an intact virus or a viral capsid, can be comprised in the cell in an episomal form or can be present integrated in a cellular DNA molecule, such as a chromosome of the cell. In a further aspect, the viral nucleic acid is an mRNA encoded by a viral gene or a cDNA molecule derived from such an mRNA. In one aspect, the target nucleic acid is derived from a human papillomavirus. In a one aspect, the automated method is a method of screening clinical samples for the presence of a high-risk human papillomavirus.

The methods disclosed herein are particularly advantageous in that they can be fully automated. Using a surface comprising carboxylated moieties in particular in form of magnetic beads comprising carboxylated moieties allows cell isolation, lysis, and nucleic acid analysis to be performed without a centrifugation step, thereby permitting a high-throughput sample processing and analysis.

In a further aspect an automated system for use in analyzing samples is provided, said system comprising: (1) a paramagnetic, superparamagnetic, ferromagnetic or ferrimagnetic carboxylated surface for use in binding cells from a liquid sample for analysis; (2) at least one magnet adapted to immobilize the carboxylated surface; (3) at least one aspiration unit adapted to remove a liquid from the carboxylated surface; (4) at least one reagent supply unit adapted to contact the carboxylated surface with at least one reagent; and (5) an analytical unit adapted to perform an analytical test on the sample. By way of example and not limitation, the reagent supply unit may be adapted to provide, for example, a lysis buffer; a wash buffer; and/or an analytical reagent, such as a nucleic acid amplification reagent, an antibody solution, or a luminescence reagent. By way of example and not limitation, the analytical unit may be a thermocycler suitable for performing real-time PCR, a fluorimeter suitable for performing fluorescence detection and quantification, or analytic units suitable for colorimetric analysis.

Detecting a Released Protein

In one aspect, the biomolecule is a protein. The released protein may optionally be further purified before or during detection. Protein purification methods include without limitation ammonium sulfate precipitation, differential solubilization, sucrose gradient centrifugation, immunoprecipitation, and chromatography. Chromatographic protein isolation methods include without limitation size exclusion, ion exchange, hydrophobic interaction, affinity, immunoaffinity, and metal binding chromatography. Proteins obtained with the disclosed methods and compositions may be used in subsequent molecular analytical methods including without limitation sequencing, immunoprecipitation, western blots, ELISA assays, dot blots, and enzyme-activity assay, such as assays for kinase activity or phophatase activity.

By way of example and not limitation, the biomolecule detected in the lysate is a peptide or protein. By way of example and not limitation, the protein may be measured using immunological methods, such as ELISA, ELISPOT, Western Blot. By way of example and not limitation, the protein may be detected by enzyme activity assays.

In a further aspect an automated system for use in analyzing samples is provided, said system comprising: (1) a paramagnetic, superparamagnetic, ferromagnetic or ferrimagnetic carboxylated surface for use in binding cells from a liquid sample for analysis; (2) at least one magnet adapted to immobilize the carboxylated surface; (3) at least one aspiration unit adapted to remove a liquid from the carboxylated surface; (4) at least one reagent supply unit adapted to contact the carboxylated surface with at least one reagent; and (5) an analytical unit adapted to perform an analytical test on the sample. By way of example and not limitation, the reagent supply unit may be adapted to provide, for example, a lysis buffer; a wash buffer; and/or an analytical reagent, such as a nucleic acid amplification reagent, an antibody solution, or a luminescence reagent. By way of example and not limitation, the analytical unit may be a fluorimeter suitable for performing fluorescence detection and quantification, a mass spectrometer, or an analytic unit suitable for colorimetric analysis such as ELISAs.

EXAMPLES

Example 1

A total of 30,000 or 300,000 SiHa cells (2 copies HPV 16 per cell) were spiked into 3 mL of clean PRESERVCYT™ ("clean PC") liquid cytology medium or HPV-negative cervical specimen pool. Each sample was then processed according to either Protocol 1 or Protocol 2, set forth below.

Protocol 1: 30 µL of SERADYN® DS-MGCM magnetic beads (50 mg/mL stock; carboxyl content: ~0.5 mEq/g; 1 µm dia.; 5% solids) were added to each 3 mL sample, and incubated at room temperature for 30 minutes. The sample was then placed on a magnetic stand and the supernatant was removed from the beads by aspiration. The beads were then resuspended in 150 µL of a 2:1 mixture of Sample Transfer Medium ("STM") (a buffered solution comprising 1 M guanidinium-HCL; 10 mM EDTA; 10 mM Tris-HCl, pH-8.2-8.6; 0.05% sodium azide) and Denaturation Reagent ("DNR") (aqueous sodium hydroxide solution comprising 1.75 M NaOH in deionized water) and incubated for 45 minutes at 65° C. to lyse the cell and release the nucleic acids. An HC2™ assay (Qiagen Gaithersburg, Inc., Gaithersburg, Md.) was then used to detect HPV16 DNA. The HC2™ Test is a nucleic acid hybridization assay with signal amplification that utilizes microplate chemiluminescent detection. Specimens containing the target DNA hybridize with a specific HPV RNA probe cocktail. The resultant RNA:DNA hybrids are captured onto the surface of a microplate well coated with antibodies specific for RNA: DNA hybrids. Immobilized hybrids are then reacted with alkaline phosphatase conjugated antibodies specific for the RNA:DNA hybrids, and detected with a chemiluminescent substrate. The intensity of the light emitted denotes the presence or absence of target DNA in the specimen. An RLU measurement equal to or greater than the Cutoff Value (CO) indicates the presence of HPV DNA sequences in the specimen. An RLU measurement less than the Cutoff Value indicates the absence of the specific HPV DNA sequences tested or HPV DNA levels below the detection limit of the assay.

Protocol 2 (Comparative): 300 µL of sample conversion buffer was added to each 3 mL sample. Sample conversion buffer is part of a commercial kit, 5100-1400, HC2™ Sample Conversion kit (Qiagen Gaithersburg, Inc., Gaithersburg, Md.). It comprises a cell binder to help pellet the specimen cells, polyacrylic acid, and eosine dye to help visualize the pellet. The cells were then pelleted at 2900 g and the supernatant poured off. The cell pellet was then resuspended in 150 µL of a 2:1 mixture of STM and DNR and incubated for 45 minutes at 65° C. HPV16DNA was then detected using an HC2™ assay as described in Protocol 1.

Figure 1:
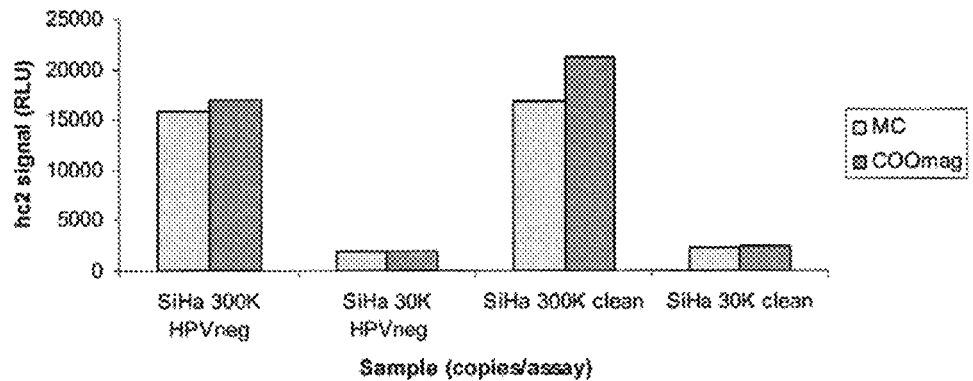

Results comparing Protocol 1 and Protocol 2 are shown in FIG. 1.

Example 2

Example 1 was repeated using the following samples: (1) 10,000 SiHa in HPV-negative PC cervical sample; (2) 5,000 SiHa in HPV-negative PC cervical sample; (3) 2,500 SiHa in HPV-negative PC cervical sample; (4) HPV-negative PC cervical sample (SiHa-free); and (5) 5,000 SiHa in clean PC.

Figure 2:
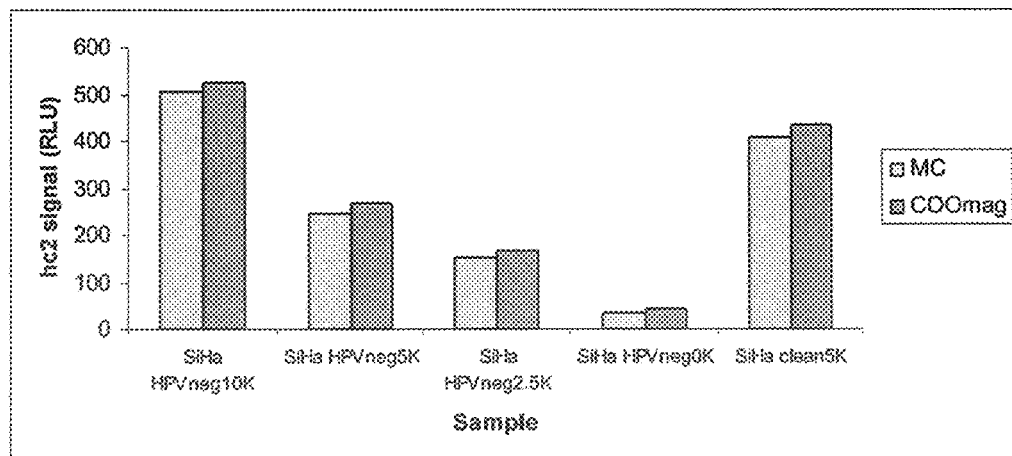

Results comparing protocol 1 and protocol 2 are shown in FIG. 2.

Example 3

Figure 3:
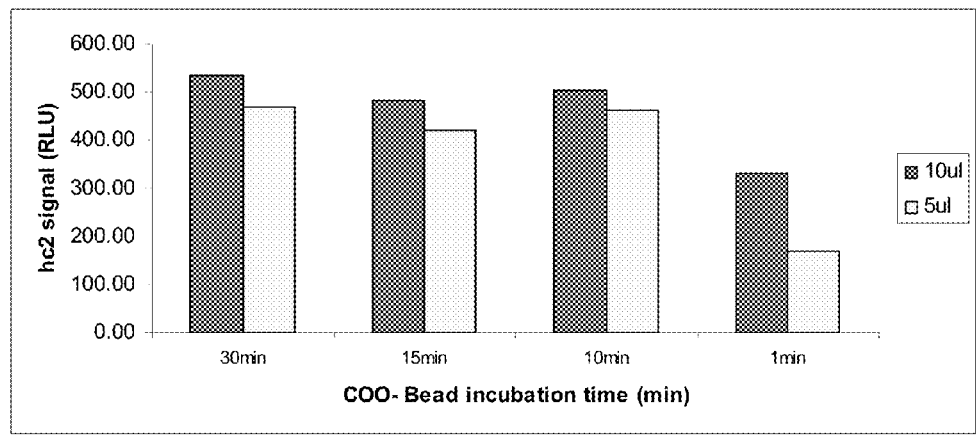

Protocol 1 was repeated with two different amount of beads added (10 µl and 5 µl) and different incubation times (1, 10, 15 and 30 min). Results are shown at FIG. 3.

Example 4

Figure 4:
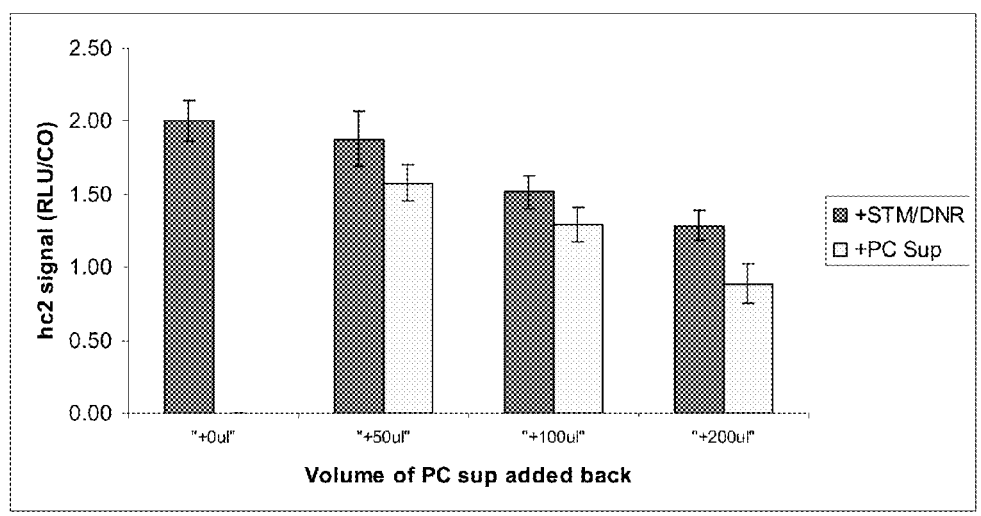

Protocol 1 was repeated using 10 µl of beads, with the proviso that various volumes (50, 100, and 200 µl) of the supernatant removed after immobilization of the cells was reserved and added back to the lysate. Equal volumes of 2:1 STM:DNR were used as controls. Results are shown at FIG. 4. Although addition of supernatant affected overall signal, the assay can nonetheless be performed without completely separating the cells from the sample.

Example 5

A total of 10,000 or 20,000 SiHa cells (2 copies HPV 16 per cell) preserved in SUREPATH™ ("SP") liquid cytology medium were spiked into a 3 mL SP HPV-negative cervical specimen pool. Each sample was then processed according to either Protocol 3 or Protocol 4, set forth below.

Protocol 3: 10 µL of SERADYN® DS-MGCM magnetic beads (50 mg/mL stock; carboxyl content: ~0.5 mEq/g; 1 µm dia.; 5% solids) were added to each 3 mL sample, and incubated at room temperature for 10 minutes with shaking (900 rpm). The sample was then placed on a magnetic stand and the supernatant was removed from the beads by aspiration. The beads were then resuspended in 150 µL of a 2:1 mixture of Sample Transfer Medium ("STM") (a buffered solution comprising guanidinium hydrochloride) and Denaturation Reagent ("DNR") (aqueous sodium hydroxide) and incubated for 45 minutes at 65° C., vortexed, and then incubated for an additional 45 minutes at 65° C. to lyse the cell and release the nucleic acids. An HC2™ assay (Qiagen Gaithersburg, Inc., Gaithersburg, Md.) was then used to detect HPV16 DNA.

Protocol 4 (Comparative): 300 µL of sample conversion buffer was added to each 3 mL sample. Sample conversion buffer is part of a commercial kit, 5100-1400, HC2™ Sample Conversion kit (Qiagen Gaithersburg, Inc., Gaithersburg, Md.). It comprises a cell binder to help pellet the specimen cells, polyacrylic acid, and eosine dye to help visualize the pellet. The cells were then pelleted at 2900 g and the supernatant poured off. The cell pellet was then resuspended in 150 µL of a 2:1 mixture of STM and DNR and incubated for 45 minutes at 65° C. HPV16 DNA was then detected using an HC2™ assay as described in Protocol 1.

Figure 5A:
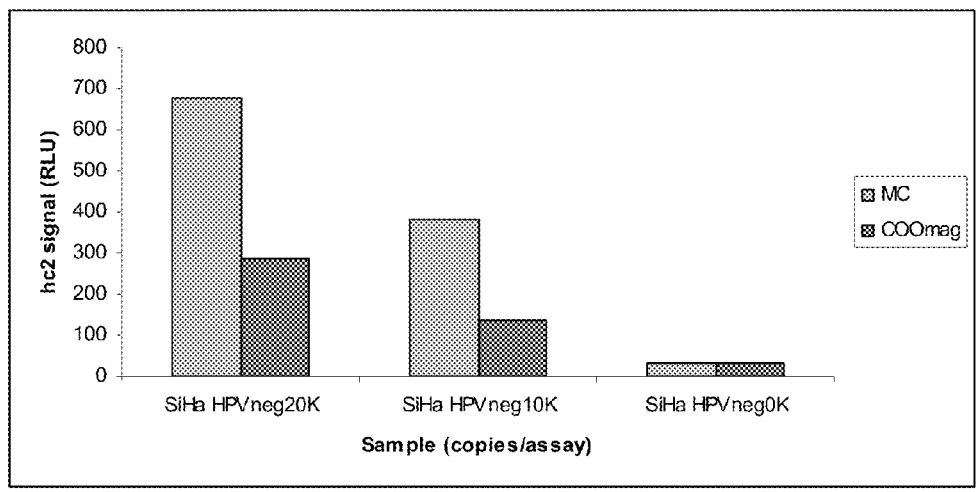
FIG. 5A and FIG. 5B are bar graphs comparing HPV16 nucleic acid recovery using carboxylate beads to concentrate 20,000, 10,000, and 0 SiHa cells spiked in SUREPATH® HPV negative cervical samples. "MC" indicates that samples were processed according to Protocol 4, while "COO—" indicates that samples were processed according to Protocol 3.
Figure 5B:
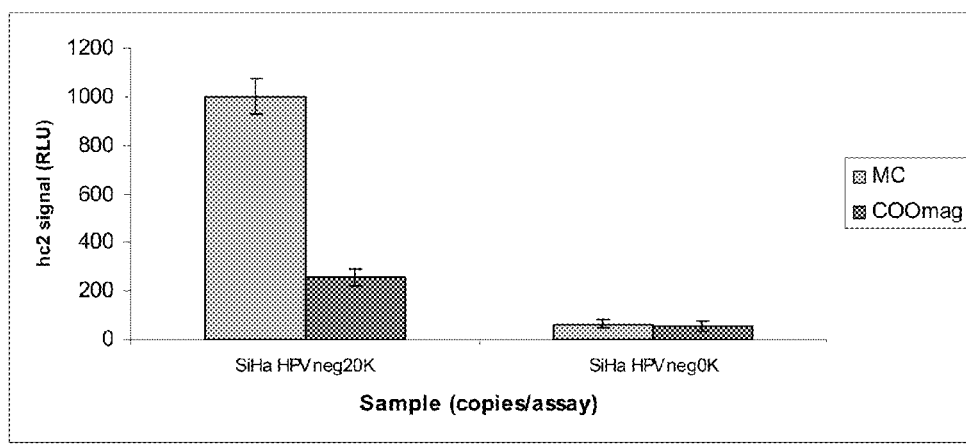

Results comparing Protocol 3 and Protocol 4 are shown in FIGS. 5A and 5B.

Example 6

Figure 6:
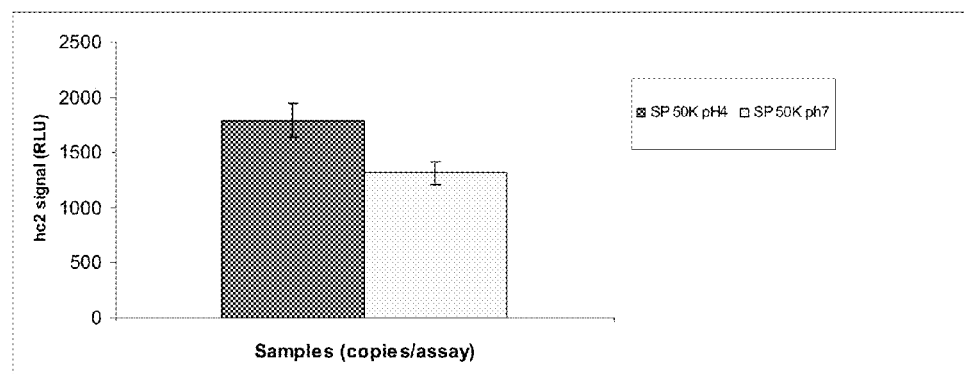
FIG. 6 is a bar graph comparing HPV16 nucleic acid recovery in SUREPATH® samples at pH 4 or pH 7.

Protocol 3 was repeated as above, except 50,000 SiHa cells were used and the pH of the SP clinical pools was brought down to pH 4 using HCl. Results are shown at FIG. 6. As can be seen, reducing the pH improved the ability of the carboxylated surface to bind to the cells.

Example 7

Figure 7:
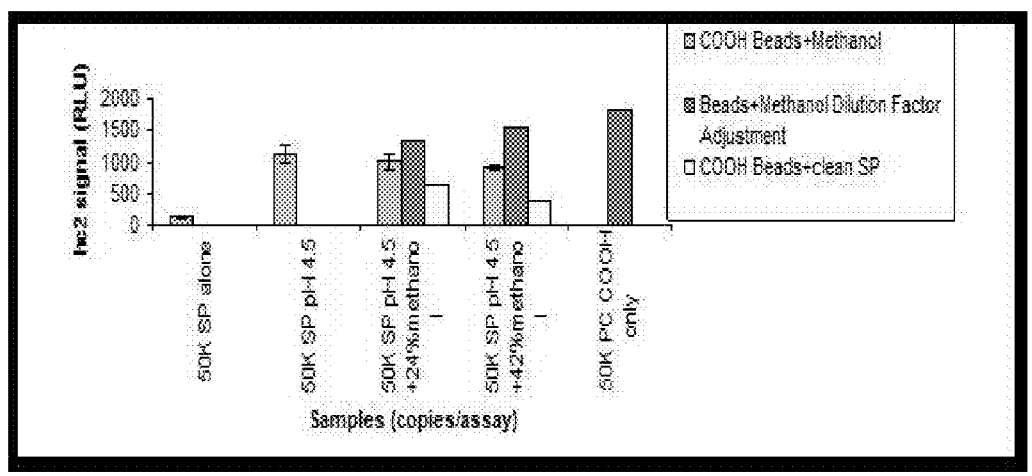
FIG. 7 is a bar graph comparing HPV16 nucleic acid recovery in SUREPATH® samples at pH 4.5 or pH 7, with or without methanol (at 24% and 42%). "SP" indicates a sample in SUREPATH®, while "PC" indicates a sample in PRESERVCYT™, which was used as a positive control.

Protocol 3 was repeated as above, except 50,000 SiHa cells were used, SP clinical pools were diluted with various volumes of methanol (24%, 42%) and the pH was brought down to pH4.5 using HCl. Results are shown at FIG. 7.

Example 8

A total of 50,000 heat inactivated *Chlamydia trachomatis* elementary bodies (5 cryptic plasmid copies per cell; 250,000 copies per assay) were spiked into 3 mL of clean PRESERVCYT™ ("clean PC") liquid cytology medium or HPV-negative cervical specimen pool in PRESERVCYT™. Each sample was then processed according to Protocol 5, set forth below.

Protocol 5: 10 µL of SERADYN® DS-MGCM magnetic beads (50 mg/mL stock; carboxyl content: ~0.5 mEq/g; 1 µm dia.; 5% solids) were added to each 3 mL sample, and incubated at room temperature for 10 minutes with shaking at 900 rpm. The sample was then placed on a magnetic stand and the supernatant was removed from the beads by aspiration and saved for processing according to protocol 6, below. The beads were then resuspended in 150 µL of a 2:1 mixture of Sample Transfer Medium ("STM") (a buffered solution comprising guanidinium hydrochloride) and Denaturation Reagent ("DNR") (aqueous sodium hydroxide) and incubated for 45 minutes at 65° C. to lyse the cell and release the nucleic acids. 75 µl of each sample was then assayed using a *Chlamydia trachomatis* specific HC2™ assay.

Protocol 6 (Comparative): 300 µL of sample conversion buffer was added to each supernatant from Protocol 5. The cells were then pelleted at 2900 g and the supernatant poured off. The cell pellet was then resuspended in 150 µL, of a 2:1 mixture of STM and DNR and incubated for 45 minutes at 65° C. 75 µL of each sample was then assayed using a *Chlamydia trachomatis* specific HC2™ assay.

Results comparing Protocol 5 and Protocol 6 are shown in FIG. 8.

Example 9

50,000 *Chlamydia trachomatis* elementary bodies (5 cryptic plasmid copies per cell; 250,000 copies per assay) were spiked into 3 mL of an HPV-negative cervical specimen pool in PRESERVCYT™ or fresh urine (stored less than 24 hours at 4° C.). Each sample was then processed according to Protocol 5 or Protocol 6, set forth below. *Chlamydia trachomatis* elementary bodies added directly to a 2:1 mixture of STM and DNR were used as a positive control.

Protocol 7: 10 µL, of SERADYN® DS-MGCM magnetic beads (50 mg/mL stock; carboxyl content: ~0.5 mEq/g; 1 µm dia.; 5% solids) were added to each 3 mL sample, and incubated at room temperature for 10 minutes with shaking at 900 rpm. The sample was then placed on a magnetic stand and the supernatant was removed from the beads by aspiration and saved for processing according to protocol 6, below. The beads were then resuspended in 150 µL of a 2:1 mixture of Sample Transfer Medium ("STM") (a buffered solution comprising guanidinium hydrochloride) and Denaturation Reagent ("DNR") (aqueous sodium hydroxide) and incubated for 45 minutes at 65° C. to lyse the cell and release the nucleic acids. 75 µL of each sample was then assayed using a *Chlamydia trachomatis* specific HC2™ assay.

Protocol 8 (Comparative): 300 µL of sample conversion buffer was added to each sample. The cells were then pelleted at 2900 g and the supernatant poured off. The cell pellet was then resuspended in 150 µL, of a 2:1 mixture of STM and DNR and incubated for 45 minutes at 65° C. 75 µL of each sample was then assayed using a *Chlamydia trachomatis* specific HC2™ assay.

Results comparing Protocol 7 and Protocol 8 are shown in FIG. 9.

The invention claimed is:

1. A method of immobilizing a cell comprising adjusting the pH of a sample comprising the cell and a liquid-based cytology medium with a pH of 7 to a pH of 4 or 4.5 and contacting a carboxylated surface with the sample for a sufficient time to permit the cell to bind to the carboxylated surface.

2. The method of claim 1, wherein the carboxylated surface is provided by solid particles having an average size of 5 µm or less.

3. The method of claim 2, wherein the solid particles are magnetic.

4. The method of claim 1, wherein the carboxylated surface has a negative overall charge.

5. The method of claim 4, wherein the carboxylated surface comprises a carboxyl content of at least 0.1 mEq/g, as determined by conductometric titration with sodium hydroxide.

6. The method of claim 5, wherein the carboxylated surface comprises a carboxyl content of 0.1 to 0.7 mEq/g, as determined by conductometric titration with sodium hydroxide.

7. The method of claim 1, wherein the liquid-based cytology medium comprises a cross-linking or non-cross-linking fixative.

8. The method of claim 1, wherein the cell is a mammalian cell.

9. The method of claim 1, wherein the carboxylated surface is suitable for cation exchange chromatography.

10. The method of claim 1, wherein binding of the cell to the carboxylated surface is not mediated by a ligand-receptor interaction or an antibody-antigen interaction.

11. The method of claim 1, wherein binding is mediated by a direct interaction between the cell and a carboxyl group of the carboxylated surface.

12. A method of isolating a cell from a sample, the method comprising:
(a) immobilizing the cell to a carboxylated surface according to the method of claim 1; and
(b) separating the carboxylated surface from at least a portion of the sample, thereby isolating the cell.

13. A method of releasing a biomolecule from a cell, the method comprising:
(b) isolating the cell according to the method of claim 12; and
(c) contacting the isolated cell with a liquid composition suitable for releasing the biomolecule from the cell.

14. The method of claim 13, wherein the liquid composition lyses the cell, thereby releasing the biomolecule.

15. The method of claim 13, wherein the biomolecule is a nucleic acid or a protein.

16. A method of determining the presence of a target nucleic acid in a sample comprising:
- (c) releasing the target nucleic acid from a cell comprised in the sample according to the method of claim 15; and
- (d) optionally, denaturing the released target nucleic acid; and
- (e) detecting the target nucleic acid by a method comprising:
  - (e1) contacting the released and optionally denatured target nucleic acid with one or more probes specific for the target nucleic acid under conditions that allow the probes and target nucleic acid to hybridize forming double-stranded nucleic acid hybrids; and
  - (e2) detecting the presence or absence of double-stranded nucleic acid hybrids.

17. The method of claim 16, wherein the carboxylated surface is disposed on a magnetic particle.

18. The method of claim 17, wherein the nucleic acid probe is hybridized to the target nucleic acid in the presence of the magnetic particle.

19. The method of claim 18, wherein the double stranded nucleic acid hybrids are detected by a method comprising:
- (e2α) capturing the double stranded nucleic acid hybrids to a solid support;
- (e2β) optionally separating the double-stranded nucleic acid hybrids bound to the solid support from un-bound nucleic acids; and
- (e2γ) detecting the presence or absence of double-stranded nucleic acid hybrids.

20. The method of claim 19, wherein:
- (e2α) the double stranded nucleic acid hybrids are captured to the solid support by contacting the double stranded hybrids with a first binding agent that is bound to or adapted to be bound to the solid phase to form a double-stranded nucleic acid/first binding agent complex; and
- (e2γ) the presence or absence of double-stranded nucleic acid hybrids is detected by (a) binding said double-stranded nucleic acid/first binding agent complex with a further binding agent that is labelled with a detectable marker to form a double-stranded nucleic acid hybrid/first binding agent/labelled binding agent complex; (b) optionally washing the double-stranded nucleic acid hybrid/first binding agent/labelled binding agent complex; and (c) detecting the presence or absence of the label of the further binding agent thereby indicating the presence or absence of the target nucleic acid.

21. The method of claim 20, wherein the solid support is coated with the first binding agent.

22. The method of claim 16, wherein at least one of (a), (b), (c), (d), or (e) is automated.

23. The method of claim 16, wherein the target nucleic acid is a viral nucleic acid, the presence of which is indicative of an viral-related disease.

24. The method of claim 16, wherein the double stranded nucleic acid hybrids are DNA:RNA hybrids.

* * * * *